United States Patent
Byrd et al.

(10) Patent No.: US 7,314,446 B2
(45) Date of Patent: Jan. 1, 2008

(54) METHOD AND APPARATUS FOR TIME GATING OF MEDICAL IMAGES

(75) Inventors: Charles Bryan Byrd, Medford, NJ (US); Praveen Dala-Krishna, Bensalem, PA (US)

(73) Assignee: EP MedSystems, Inc., West Berlin, NJ (US)

(*) Notice: Subject to any disclaimer, the term of this patent is extended or adjusted under 35 U.S.C. 154(b) by 259 days.

(21) Appl. No.: 11/002,661

(22) Filed: Dec. 3, 2004

(65) Prior Publication Data

US 2005/0080336 A1 Apr. 14, 2005

Related U.S. Application Data

(63) Continuation-in-part of application No. 10/620,517, filed on Jul. 16, 2003, now Pat. No. 7,211,045.

(60) Provisional application No. 60/397,653, filed on Jul. 22, 2002.

(51) Int. Cl.
*A61B 8/00* (2006.01)
(52) U.S. Cl. ..................... 600/443
(58) Field of Classification Search ........ 600/443–447, 600/454–456, 458, 439, 513; 128/916
See application file for complete search history.

(56) References Cited

U.S. PATENT DOCUMENTS

| | | | |
|---|---|---|---|
| 4,161,121 A | 7/1979 | Zitelli et al. | |
| 4,241,610 A | 12/1980 | Anderson | |
| 4,462,408 A | 7/1984 | Silverstein et al. | |
| 4,519,260 A | 5/1985 | Fu et al. | |
| 4,576,177 A | 3/1986 | Webster, Jr. | |
| 4,605,009 A | 8/1986 | Pourcelot et al. | |
| 4,841,977 A | 6/1989 | Griffith et al. | |
| 4,890,268 A | 12/1989 | Smith et al. | |
| 4,917,097 A | 4/1990 | Proudian et al. | |
| 4,951,677 A | 8/1990 | Crowley et al. | |
| 5,002,059 A | 3/1991 | Crowley et al. | |
| 5,090,956 A | 2/1992 | McCoy | |
| 5,105,819 A | * 4/1992 | Wollschlager et al. | 600/463 |
| 5,152,294 A | 10/1992 | Mochizuki et al. | |
| 5,170,793 A | 12/1992 | Takano et al. | |
| 5,195,968 A | 3/1993 | Lundquist et al. | |

(Continued)

OTHER PUBLICATIONS

Keith S. Dickerson et al., "Comparison of Conventional and Transverse Doppler Sonograms", J. Ultrasound Med., 1993, pp. 497-506, vol. 12.

(Continued)

*Primary Examiner*—Francis J. Jaworski
(74) *Attorney, Agent, or Firm*—Hansen Huang Tech. Law Group LLP (57) ABSTRACT

A medical imaging system is provided which includes a signal generator configured to obtain a trigger signal corresponding to a timing of interest, imaging equipment configured to obtain a plurality of images of a feature of interest, and a processor programmed to correlate the plurality of images with the trigger signal. Also provided is a method of correlating a plurality of medical images by obtaining a trigger signal of a timing of interest, obtaining a plurality of images of a feature of interest, and correlating the plurality of images with the trigger signal.

15 Claims, 5 Drawing Sheets

U.S. PATENT DOCUMENTS

| | | | |
|---|---|---|---|
| 5,254,088 A | 10/1993 | Lundquist et al. | |
| 5,279,559 A | 1/1994 | Barr | |
| 5,307,816 A | 5/1994 | Hashimoto et al. | |
| 5,309,914 A | 5/1994 | Iinuma | |
| 5,325,860 A | 7/1994 | Seward et al. | |
| 5,336,182 A | 8/1994 | Lundquist et al. | |
| 5,345,938 A | 9/1994 | Nishiki et al. | |
| 5,345,940 A | 9/1994 | Seward et al. | |
| 5,357,550 A * | 10/1994 | Asahina et al. | 378/98.5 |
| 5,358,478 A | 10/1994 | Thompson et al. | |
| 5,364,351 A | 11/1994 | Heinzelman et al. | |
| 5,395,327 A | 3/1995 | Lundquist et al. | |
| 5,456,258 A | 10/1995 | Kondo et al. | |
| 5,456,664 A | 10/1995 | Heinzelman et al. | |
| 5,499,630 A | 3/1996 | Hiki et al. | |
| 5,515,853 A * | 5/1996 | Smith et al. | 600/437 |
| 5,531,686 A | 7/1996 | Lundquist et al. | |
| 5,560,362 A | 10/1996 | Sliwa, Jr. et al. | |
| 5,588,432 A * | 12/1996 | Crowley | 600/439 |
| 5,662,116 A | 9/1997 | Kondo et al. | |
| 5,697,965 A | 12/1997 | Griffin, III | |
| 5,699,805 A | 12/1997 | Seward et al. | |
| 5,704,361 A | 1/1998 | Seward et al. | |
| 5,713,363 A | 2/1998 | Seward et al. | |
| 5,715,817 A | 2/1998 | Stevens-Wright et al. | |
| 5,722,403 A * | 3/1998 | McGee et al. | 600/373 |
| 5,749,364 A | 5/1998 | Sliwa, Jr. et al. | |
| 5,788,636 A | 8/1998 | Curley | |
| 5,795,299 A | 8/1998 | Eaton et al. | |
| 5,797,848 A | 8/1998 | Marian et al. | |
| 5,807,324 A | 9/1998 | Griffin, III | |
| 5,846,205 A | 12/1998 | Curley et al. | |
| 5,888,577 A | 3/1999 | Griffin, III et al. | |
| 5,891,088 A | 4/1999 | Thompson et al. | |
| 5,906,579 A | 5/1999 | Vander Salm et al. | |
| 5,921,978 A | 7/1999 | Thompson et al. | |
| 5,928,276 A | 7/1999 | Griffin, III et al. | |
| 5,931,863 A | 8/1999 | Griffin, III et al. | |
| 5,935,102 A | 8/1999 | Bowden et al. | |
| 5,938,616 A | 8/1999 | Eaton et al. | |
| 5,954,654 A | 9/1999 | Eaton et al. | |
| 6,013,072 A | 1/2000 | Winston et al. | |
| 6,033,378 A | 3/2000 | Lundquist et al. | |
| 6,039,693 A | 3/2000 | Seward et al. | |
| 6,085,117 A | 7/2000 | Griffin, III et al. | |
| 6,144,870 A | 11/2000 | Griffin, III | |
| 6,171,248 B1 | 1/2001 | Hossack et al. | |
| 6,173,205 B1 | 1/2001 | Griffin, III et al. | |
| 6,210,333 B1 * | 4/2001 | Gardner et al. | 600/450 |
| 6,224,556 B1 | 5/2001 | Schwartz et al. | |
| 6,228,028 B1 | 5/2001 | Klein et al. | |
| 6,228,032 B1 | 5/2001 | Eaton et al. | |
| 6,306,096 B1 | 10/2001 | Seward et al. | |
| 6,306,097 B1 | 10/2001 | Park et al. | |
| 6,310,828 B1 | 10/2001 | Mumm et al. | |
| 6,360,027 B1 | 3/2002 | Hossack et al. | |
| 6,368,275 B1 | 4/2002 | Sliwa et al. | |
| 6,385,489 B1 | 5/2002 | Griffin, III et al. | |
| 6,398,731 B1 | 6/2002 | Mumm et al. | |
| 6,423,002 B1 | 7/2002 | Hossack | |
| 6,440,488 B2 | 8/2002 | Griffin, III et al. | |
| 6,443,894 B1 | 9/2002 | Sumanaweera et al. | |
| 6,475,148 B1 | 11/2002 | Jackson et al. | |
| 6,475,149 B1 | 11/2002 | Sumanaweera | |
| 6,482,161 B1 | 11/2002 | Sumanaweera et al. | |
| 6,485,455 B1 | 11/2002 | Thompson et al. | |
| 6,491,633 B1 | 12/2002 | Krishnan et al. | |
| 6,503,202 B1 | 1/2003 | Hossack et al. | |
| 6,517,488 B1 | 2/2003 | Hossack | |
| 6,527,717 B1 | 3/2003 | Jackson et al. | |
| 6,532,378 B2 | 3/2003 | Saksena et al. | |
| 6,554,770 B1 | 4/2003 | Sumanaweera et al. | |
| 6,589,182 B1 | 7/2003 | Loftman et al. | |
| 6,605,043 B1 | 8/2003 | Dreschel et al. | |
| 6,607,488 B1 | 8/2003 | Jackson et al. | |
| 6,612,992 B1 | 9/2003 | Hossack et al. | |
| 6,645,147 B1 | 11/2003 | Jackson et al. | |
| 6,648,875 B2 | 11/2003 | Simpson et al. | |
| 6,709,396 B2 | 3/2004 | Flesch et al. | |
| 2003/0045796 A1 | 3/2003 | Friedman | |
| 2003/0158483 A1 | 8/2003 | Jackson et al. | |

OTHER PUBLICATIONS

David J. Sahn, "Phased Arrays for Multiplane Esophageal Echos in Infants", Summary Statement, Diagnostic Radiology Study Section, Jun. 1990.

David J. Sahn, "Instrumentation and Physical Factors Related to Visualization of Stenotic and Regurgitant Jets by Doppler Color Flow Mapping", JACC, Nov. 1988, pp. 1354-1365, vol. 12, No. 5.

David J. Sahn, "Advances in Ultrasound Imaging for Congenital Heart Disease Diagnosis and Management", Pediatric Cardiology, Nov. 26-Dec. 1, 1989, Proceedings of the III World Congress of Pediatric Cardiology, Bangkok.

David J. Sahn et al., "Important Rolesof Transeophageal Color Doppler Flow Mapping Studies(TEE) in Infants with Congenital Heart Disease", Supplement to Journal of the American College of Cardiology, Feb. 1990, vol. 15, No. 2 (Supplement A).

David J. Sahn, "Applications of Color Flow Mapping in Pediatric Cardiology", Cardiology Clinics, May 1989, pp. 255-264, vol. 7, No. 2.

David J. Sahn, et al., "Miniaturized High Frequency Phased Array Devices for High Resolution Neonatal and Intraoperative Imaging", Supplement to Journal of the American College of Cardiology, Feb. 1990, vol. 15, No. 2 (Supplement A).

Piero Tortoli et al., "Velocity Magnitude Estimation with Linear Arrays Using Doppler Bandwidth", Ultrasounics, 2001, pp. 157-161, vol. 39.

Lilliam M. Valdes-Cruz et al., "Transvascular Intracardiac Applications of a Miniaturized Phase-Array Ultrasonic Endoscope", Brief Rapid Communication, Mar. 1991, pp. 1023-1027, vol. 83, No. 3.

Lilliam M. Valdes-Cruz et al., "Experimental Animal Investigations of the Potential for New Approaches to Diagnostic Cardiac Imaging in Infants and Small Premature Infants from Intracardiac and Trasesophageal Approaches Using a 20MHz Real Time Ultrasound Imaging Catheter", Supplement to Journal of the American College of Cardiology, Feb. 1989, vol. 13, No. 2 (Supplement A).

P.N.T. Wells, "Velocity, Absorption and Attenuation in Biological Materials", Biomedical Ultrasonics, 1977, pp. 110-144.

Antonio L. Bartorelli, M.D. et al., "Plaque Characterization of Atherosclerotic Coronary Arteries by Intravascular Ultrasound", Echocardiography: A Journal of CV Ultrasound & Allied Tech, 1990, pp. 389-395, vol. 7, No. 4.

N. Bom et al., "Early and recent intraluminal ultrasound devices", International Journal of Cardiac Imaging, 1989, pp. 79-88, vol. 4.

R.J. Crowley et al., "Optimized ultrasound imaging catheters for use in the vascular system", International Journal of Cardiac Imaging, 1989, pp. 145-151, vol. 4.

R.J. Crowley, et al., "Ultrasound guided therapeutic catheters: recent developments and clinical results", International Journal of Cardiac Imaging, 1991, pp. 145-156, vol. 6.

Richard A. Carleton, M.D., et al., "Measurement of Left Ventricular Diameter In the Dog by Cardiac Catheterization", Circulation Research, May 1968, pp. 545-558, vol. XXII.

Taher Elkadi et al., "Importance of Color Flow Doppler (CFD) Imaging of the Right Ventricular Outflow Tract and Pulmonary Arteries by Transesophageal Echocardiography (TEE) During Surgery for CHD", Supplement III Circulation, Oct. 1990, p. III-438, vol. 82, No. 4.

Philip C. Currie, "Transeosphageal Echocardiography New Window to the Hearth", Circulation, Jul. 1989, pp. 215-217, vol. 88, No. 1.

Steven Schwartz et al., "In Vivo Intracardiac 2-D Echocardiography: Effects of Transducer Frequency, Imaging Approached and Comparison with Fiberoptic Angioscopy", JACC, Feb. 1990, pp. 29A, vol. 15, No. 2.

J. Souquet et al., "Transesophageal Phased Array for Imaging the Heart", IEEE Transactions on Biomedical Engineering, Oct. 1982, pp. 707-712, vol. BME-29, No. 10.

Craig J. Hartley, "Review of Intracoronary Doppler catheters", International Journal of Cardiac Imaging, 1989, pp. 159-168, vol. 4.

John McB. Hodgson et al., "Percutaneous Intravascular Ultrasound Imaging: Validation of a Real-Time Synthetic Aperture Array Catheter", American Journal of Cardiac Imaging, Mar. 1991, pp. 56-71, vol. 5, No. 1.

J. McB. Hodgson et al., "Clinical percutaneous imaging of corconary anatomy using an over-the-wire ultrasound catheter system", International Journal of Cardiact Imaging, 1989, pp. 187-193, vol. 4.

Brenda S. Kusay et al., "Realtime in Vivo Intracardiac Two-Dimensional Echocardiography and Color Flow Imaging: Approaches, Imaging Planes, and Echo Anatomy", Abstracts of the 62nd Scientific Sessions, 1989, p. II-581.

Charles T. Lancee, "A Transesophageal Phased Array Transducer for Ultrasonic Imaging of the Heart", 1987.

Natesa Pandian et al., "Enhanced Depth of Field in Intracardiac 2-D Echocardiography with a New Prototype, Low Frequency (12 MHz, 9 French) Ultrasound Catheter", Supplemental III Circulation, Oct. 1990, p. III-442, vol. 82, No. 4.

Natesa G. Pandian, M.D. et al., "Intravascular and Intracardiac Ultrasound Imaging: Current Research and Future Directions", Echocardiography: A Journal of CV Ultrasound & Allied Tech., 1990, pp. 377-387, vol. 7, No. 4.

Natesa G. Pandian, M.D. et al., "Intracardiac, Intravascular, Two-Dimensional, High-Frequency Ultrasound Imaging of Pulmonary Artery and Its Branches in Humans and Animals", Circulation, Jun. 1990, pp. 2007-2012, vol. 81, No. 6.

F. Ricou et al., "Applications of intravascular scanning and transesophageal echocardiography in congenital heart disease: tradeoffs and the merging of technologies", International Journal of Cardiac Imaging, 1991, pp. 221-231, vol. 6.

Samuel B. Ritter, M.D., et al., "Transesophageal real time Doppler flow imaging in congenital heart disease: experience with a new pediatric trasducer probe", 1989, Dynamedia, Inc.

Samuel B. Ritter, M.D., et al., "Pediatric Transesophageal Color Flow Imaging: Smaller Probes for Smaller Hearts", 1989.

David J. Sahn, M.D., et al., "Important Roles of Transesophageal Color Doppler Flow Mapping Studies (TEE) in Infants With Congenital Heart Disease", IACC, Feb. 1990, p. 204A, vol. 15, No. 2.

David J. Sahn, M.D. et al., "Miniaturized High Frequency Phased Array Devices for High Resolution Neonatal and Intraoperative Imaging", JACC, Feb. 1990, p. 10A, vol. 15, No. 2.

David J. Sahn, M.D., et al., "Phased Arrays for Multiplane Esophageal Echos in Infants", Grant Application, Department of Health and Human Services Public Health Service, 1992.

Steven Schwartz, M.D., et al., "Intracardiac Echocardioraphic Guidance and Monitoring During Aortic and Mitral Balloon Valvuloplasty", JACC, Feb. 1990, p. 104A, vol. 15, No. 2.

James B. Seward, M.D. et al., "Biplanar Transesophageal Echocardiography: Anatomic Correlations, Image Orientation, and Clinical Applications", Mayo Clin Proc., 1990, pp. 1198-1213, vol. 65.

James B. Seward, M.D. et al., "Wide-Field Transesophageal Echocardiographic Tomography: Feasibility Study", Mayo Clin Proc. 1990, pp. 31-37, vol. 65.

Khalid H. Sheikh, M.D., et al., "Interventional Applications of Intravascular Ultrasound Imaging: Initial Experience and Future Perspectives", Echocardiography: A Journal of CV Ultrasound & Allied Tech., pp. 433-441, vol. 7, No. 4, Jul. 1990.

Paul G. Yock, M.D., et al., "Two-Dimensional Intravascular Ultrasound: Technical Development and Initial Clinical Experience", Journal of American Society of Echocardiography, 1989, pp. 296-304, vol. 2, No. 4.

Paul G. Yock, M.D. et al., "Real-Time, Two-Dimensional Catheter Ultrasound: A New Technique for High-Resolution Intravascular Imaging", JACC, Feb. 1988, p. 130A, vol. 11, No. 2.

P. Yock et al., "Intravascular Two-Dimensional Catheter Ultrasound: Initial Clinical Studies", Abstracts of the 61st Scientist Sessions, p. 11-21, 1988.

Michael J. Eberle et al., "Validation of a New Real Time Percotaneous Intravascular Ultrasound Imaging Catheter", Abstracts of the 61st Scientist Sessions, p. 11-21, 1988.

Natasa Pandian et al., "Intralurolonal Ultrasound Angloscopic Detection of Arterial Dissection and Intimal Flaps: In Vitro and In Vivo Studies", Abstracts of the 61st Scientist Sessions, p. 11-21, 1988.

John A. Mallery et al., "Evaluation of an Intravascular ultrasound Imaging Catheter in Porcine Peripheral and Coronary Arteries In Vivo", Abstracts of the 61st Scientist Sessions, p. 11-21, 1988.

Andrew Wintraub, M.D., "Realtime Intracardiac Two-Dimensional Echocardiography in the Catheterization Laboratory in Humans", Intravascular Imaging I, Mar. 19, 1990.

* cited by examiner

METHOD AND APPARATUS FOR TIME GATING OF MEDICAL IMAGES

CORRESPONDING RELATED APPLICATIONS

The present invention is a continuation in part of U.S. patent application Ser. No. 10/620,517 filed on Jul. 16, 2003, entitled Method And System For Using Ultrasound In Cardiac Diagnosis And Therapy claiming priority to Provisional Application Ser. No. 60/397,653 filed on Jul. 22, 2002. The entire contents of both these applications are incorporated by reference herein in their entirety.

BACKGROUND OF THE INVENTION

1. Field of the Invention

The present invention is directed at medical imaging technology, and more particularly, to methods and apparatuses for time gating of medical images.

2. Description of the Related Art

Medical imaging technology is used to improve the diagnosis and treatment of medical conditions. Presently available medical imaging technology includes a wide variety of imaging systems, such as fluoroscopy, angiography, echocardiography, computed tomography, ultrasound, x-ray, nuclear, magnetic resonance imaging (MRI) and other imaging systems.

Recent advances in medical imaging now allow physicians to visualize moving structures, which has improved the diagnosis and treatment of many medical conditions. More specifically, by providing physicians with methods and apparatuses to see the actual movement of an object of interest, they can better diagnose conditions causing abnormal behavior. In many circumstances, ultrasound is the imaging modality of choice, especially in cardiology, since this modality offers real-time imaging capabilities of the moving heart. Further, advances through Doppler techniques allow physicians to visualize as well as measure blood flow. Pulse wave and continuous wave Doppler have proven to be quite accurate, and an effective way of evaluating flow through various parts of the circulatory system, especially the heart. Tortoli et al., *Ultrasound Med. Bio.*, 28, 249-257 (2002); Mohan et al., *Pediatr. Cardiol.* 23, 58-61 (2002); Ogawa et al., *J. Vasc. Surg.*, 35, 527-531 (2002); Pislaru et al., *J. Am. Coll. Cardiol.*, 38, 1748-1756 (2001). Further development in the area of medical imaging technology is needed, however, as existing tools are limited in functionality and capability.

Other problems with the prior art not described above can also be overcome using the teachings of the present invention, as would be readily apparent to one of ordinary skill in the art after reading this disclosure.

SUMMARY OF THE INVENTION

In an embodiment of the present invention, a medical imaging system includes a signal generator configured to obtain a trigger signal corresponding to a timing of interest, imaging equipment configured to obtain a plurality of images of a feature of interest, such as an intra-cardial chamber, and a processor programmed to correlate the plurality of images with the trigger signal. The signal generator may include at least one sensor, such as an intra-cardiac electrocardiograph (ECG) sensor, adapted and configured to sense a physiological condition of a patient, the trigger signal corresponding to a physiological condition sensed by the at least one sensor (e.g., a particular ECG signal or a periodic atrial fibrillation feature) designated automatically or by user selection. The imaging equipment comprises an intra-body ultrasound catheter, which may include a linear phased array transducer that is rotatable to provide differing fields of view. In an embodiment, the ECG sensors is positioned on the intra-body ultrasound catheter. The processor may be programmed to control the intra-body ultrasound catheter so as to acquire an ultrasound image when triggered by the trigger signal and store images, and/or to shift the obtaining of images in time by a time increment from the trigger signal. The processor also may be programmed to correlate the stored images with the trigger signal and process the correlated images, such as to generate three-dimensional images and four-dimensional moving images. A localizer may be included to determine an intra-body location of the imaging equipment.

In another embodiment a method of correlating a plurality of medical images includes obtaining a trigger signal of a timing of interest, obtaining a plurality of images of a feature of interest, and correlating the plurality of images with the trigger signal. The plurality of images may be of one or multiple locations. The images may also be localized and combined to generate a three-dimensional representation of the feature of interest. The method may also include identifying the feature of interest and tracking it in the plurality of images. Obtaining the trigger signal may be by sensing a physiological event of a patient, such as by an ECG sensor. The method may further include superimposing a 3-dimensional wire frame of a heart upon the plurality of images, and/or integrating ultrasound and fluoroscopic image data into an electronic record. Instructions for causing a processor to perform these various method steps may be stored on a computer-readable medium or within the memory of a process.

DETAILED DESCRIPTION OF THE EXEMPLARY EMBODIMENTS

Reference will now be made in detail to exemplary embodiments of the present invention. Wherever possible, the same reference numbers will be used throughout the drawings to refer to the same or like parts.

A. Exemplary Medical Imaging Systems

Figure 1:
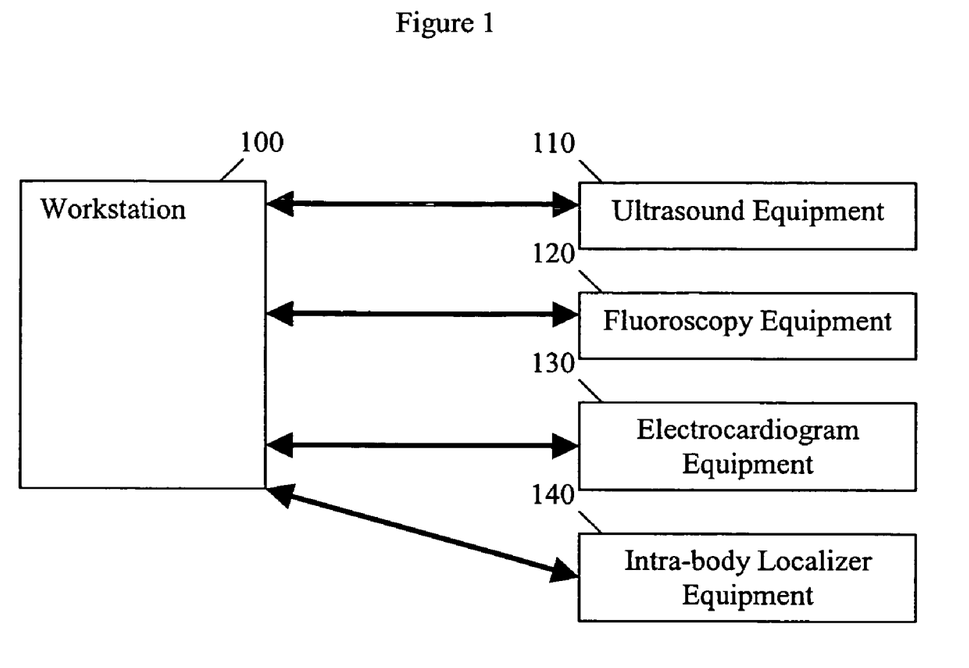
FIG. 1 is a block diagram of a medical imaging system according to an embodiment of the present invention.

An exemplary medical imaging system usable with various embodiments of the present invention is shown in the block diagram of FIG. 1. The medical imaging system comprises workstation 100, ultrasound equipment 110 (a first imaging equipment), fluoroscopy equipment 120 (a second imaging equipment), electrocardiogram (ECG)

equipment 130 (a physiological measuring equipment), and intra-body localizer equipment 140. Additional components may also be provided and/or some of the depicted components may be combined or eliminated in some embodiments, as would be readily apparent to one of ordinary skill in the art after reading this disclosure.

Preferably, first imaging equipment 110 includes a percutaneous ultrasound imaging catheter designed for intracardiac and/or intravascular use. Such a catheter is generally sized as 10 French or less, has multiple elements on the transducer (e.g., 48 or 64 elements), employs relatively low frequencies (e.g., about 5 to about 10 MHz), and uses a phased array transducer for optimal resolution. The catheter ultrasound beam may be electronically steered in two or three dimensions in an imaging plane, and most desirably is steerable in two dimensions by about 180°. Additionally, the catheter can be configured to be longitudinally side-firing circularly perpendicular to the catheter axis, though other configurations are also contemplated.

According to one aspect of the present invention, a linear phased array transducer is provided as part of the ultrasound imaging catheter, such as being positioned on or beyond a bendable portion of the catheter, preferably having a radius of curvature between about 0.25 and 2.5 inches to facilitate positioning the catheter within a patient's body, most preferably having a radius of curvature of about 1 inch. The linear phased array preferably includes between 4 and 256 transducer elements, more preferably including between 32 and 128 transducer elements, and most preferably including 64 transducer elements. Such a transducer array may have an aperture of, for example, between 3 and 30 mm, preferably between 10 and 15 mm.

For intracardiac imaging, the linear phased array preferably operates at frequencies between 2 and 25 MHz, more preferably between 4 and 10 MHz, and most preferably between 4.5 and 8.5 MHz. Such a frequency range may be stepped depending on the particular configuration implemented (e.g., to provide an adjustable imaging depth), such as at 0.5 MHz intervals. Other array configurations are also contemplated.

According to one aspect of the present invention, second imaging equipment 120 includes a non-ultrasound imaging device, such as the depicted fluoroscopy equipment or the like, the second imaging equipment 120 providing information/images in addition to or in place of those generated by first imaging equipment 110. By way of example, second imaging equipment 120 may include a fluorometer to create and place digitized X-ray images into workstation 100 for later combination with ultrasound image data based upon correlation with physiological events or features.

In this regard, a number of x-ray imaging systems may be used, such as real-time x-ray systems where x-rays are projected into an object to be x-rayed and shadows caused by relatively x-ray opaque matter within the object are detected on the fluoroscope located on the opposite side of the object from the x-ray source. Other exemplary x-ray systems involve the use of reverse-geometry x-ray imaging systems. In such systems, an x-ray tube is employed in which an electron beam is generated and focused upon a small spot on a relatively large target assembly, emitting x-ray radiation from that spot. The electron beam is deflected in a scan pattern over the target assembly. A relatively small x-ray detector is placed at a distance from the target assembly of the x-ray tube. The x-ray detector converts x-rays that strike it into an electric signal indicative of the amount of x-ray flux detected at the detector. One advantage provided by reverse-geometry systems is that the geometry of such systems allows x-rays to be projected at an object from multiple angles without requiring physical relocation of the x-ray tube.

It will be appreciated by one of ordinary skill in the art that, when an object is placed between the x-ray tube and the detector, x-rays are attenuated and/or scattered by the object in proportion to the x-ray density of the object. While the x-ray tube is in scanning mode, the signal from the detector is inversely proportional to the x-ray density of the object. The output signal from the detector can be applied to the z-axis (luminance) input of a video monitor. This signal modulates the brightness of the viewing screen. The x and y inputs to the video monitor can be derived from the signals that effect deflection of the electron beam of the x-ray tube. Therefore, the luminance of a point on the viewing screen is inversely proportional to the absorption of x-rays passing from the source, through particular areas of the object, to the detector. Other configurations are also contemplated.

According to another aspect of the present invention as shown in FIG. 1, workstation 100 preferably includes a display device, a user input device (e.g., a keyboard, mouse, touch-screen display or the like), and a programmable controller. According to an embodiment of the present invention, the programmable controller may comprise microprocessor, an application specific integrated circuit (ASIC), or the like, the programmable controller being adapted and configured to operate in accordance with one or more of the methods discussed below. Further, workstation 100 may be coupled to one or more of equipment 110, 120 and 130 via an isolation/junction box (not shown), as described in copending application Ser. No. 10/997,898 entitled "Method And Apparatus For Isolating A Catheter Interface" filed concurrently herewith and which is incorporated by reference herein in its entirety. Other configurations for workstation 100 are also contemplated.

Preferably, the workstation 100 displays medical images on one or more display devices (not shown), as well as other types of data (e.g., electrocardigram (ECG) traces) and/or equipment control parameters. In a desirable embodiment, 3-dimensional (3D) images are displayed. The display technology of 3D images used for embodiments can be divided into these categories: (1) those that provide a transparent 3D surface grid as a 3D reference; (2) those that create a true 3D image; (3) those that create an illusion of seeing a 3D image; and (4) those having further subdivisions of an image, such as into multiple parallel planar slices. The first category can provide an overlapping image for use as a model reference to compare measured data to. In a desirable embodiment, the co-display of an optimum grid with an actual measured structure, can help a user identify a structural anomaly. The second category includes holographic displays, varifocal synthesis, spinning screens and LED panels. The second category includes both computer graphics, which appeal to psychological depth cues, and stereoscopic imaging based on the mental fusing of two (left and right) retinal images. Stereoscopic imaging displays can be sub-divided into systems that require the use of special glasses, (e.g., head mounted displays and polarized filter glasses) and systems based on auto-stereoscopic technology that do not require the use of special glasses. The third category is most convenient for regular display devices such as liquid crystal displays and cathode ray tube displays. The fourth category, which can display a true image or illusion of a 3D image, provides further information of value to the user and may be used particularly for detailed analysis.

In an embodiment a 3D image is displayed on a regular 2-dimensional (2D) monitor such as a CRT or flat panel LCD display. The imaging system also can electronically vary the presentation of the orthographic projection views (i.e., the front, rear, side, top, and/or bottom views). In one such embodiment, after examining the front view and the side views, a clinician can change the orientation of the views by changing a yaw offset. A yaw output is provided to cine data processors in the controller, which re-calculate the front, side, top and/or bottom views. Icons may be generated and displayed along with the images. A variety of view manipulations can be readily ascertained and some are described in U.S. Pat. Nos. 4,468,747; 4,471,449; and 5,197,037, which are incorporated by reference herein in their entirety. Also see "Ultrasound Imaging: an Overview" and "A Scan Conversion Algorithm for Displaying Ultrasound Images", Hewlett-Packard Journal, October 1983, also all incorporated by reference herein in their entirety.

According to another aspect of the present invention as shown in FIG. 1, workstation 100 preferably includes a display device, a user input device (e.g., a keyboard, mouse, touch-screen display or the like), and a programmable controller. According to an embodiment of the present invention, the programmable controller may comprise microprocessor, an application specific integrated circuit (ASIC), or the like, the programmable controller being adapted and configured to operate in accordance with one or more of the methods discussed below. Further, workstation 100 may be coupled to one or more of equipment 110, 120 and 130 via an isolation/junction box (not shown), as described in copending application Ser. No. 10/997,898 entitled "Method And Apparatus For Isolating A Catheter Interface" filed concurrently herewith and which is incorporated by reference herein in its entirety. Other configurations for workstation 100 are also contemplated.

The class of 3D displays, termed "volumetric displays", is rapidly advancing and embodiments may be useful for showing 3 and 4-dimensional images as described herein. Displays in this type-class include holographic displays, swept volume displays and static volume displays. Volumetric displays show 3D graphical scenes within a true 3D volume. Such displays can assume many shapes including cylinders, globes, domes, cubes, an arbitrary shape, etc., with a dome being a typical shape and a desired shape can be chosen according to the needs of particular users. In an embodiment, a heart shaped display is provided. U.S. Patent Application No. 20030142067 filed by Kurtenbach provides representative examples of this technology, and is incorporated by reference herein in its entirety.

In another embodiment a 3D projection system and related method employing liquid crystal display panels and a phase screen is used to project a true three-dimensional image of an object as described, for example in U.S. Patent Application No. 20030122828 filed by Lukyanitsa, which is incorporated by reference herein in its entirety. Certain embodiments of these projection systems include an imaging system capable of projecting "amplitude hologram" images onto a phase screen to produce the viewable three-dimensional image.

In addition to 3D displays, an image may be directed to a 3D rendering system capable of generating a 3D model of the imaged structure (e.g. heart). Such 3D rendering systems known in the art include, for example, 3D laser lithography and 3D ink jet free form fabrication.

B. Exemplary Methods of Operation

As an example of the operation of the medical imaging system described above, a multi-dimensional image may be obtained from fluorometer data for use in constructing the outlines of an organ (e.g., a heart) on a display monitor. Additionally, data may be obtained from a sonic array (a part of first imaging equipment 110) and converted into a form suitable for 3D display. Preferably, this data are standardized by comparison with a 3D map and the standardized data are placed into cine file memories, accessible by workstation 100. Meanwhile, physiological data may be obtained from ECG equipment 130 and then electronically stored and indexed so that physiological measurements may be linked with 3D image measurements. Based on user input, screen images may be selected that are linked to desired physiological signal(s) and sent to the display. Other modes of operation are also contemplated, as will be described in greater detail below with reference to FIGS. 2-5.

Figure 2:
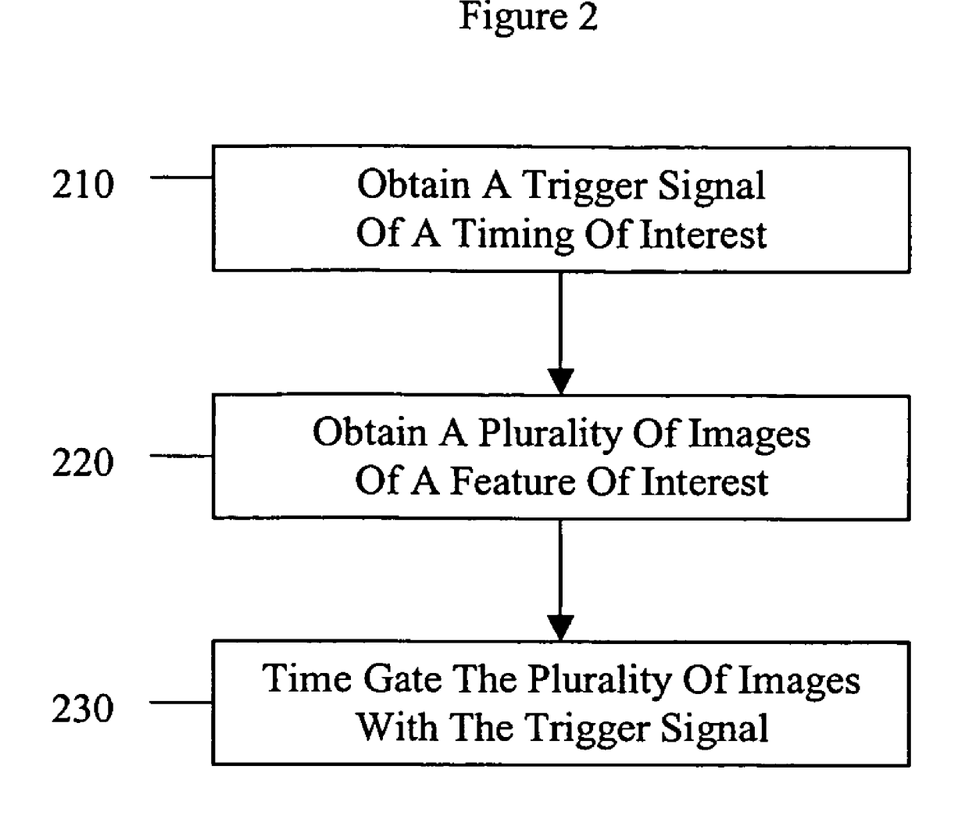
FIG. 2 is a flowchart of a method of time-gating medical images according to an embodiment of the present invention.

A method of time gating a medical image according to an embodiment of the present invention is shown in the flowchart of FIG. 2. This method may be performed using the medical imaging system depicted in FIG. 1, or with another compatible system, as would be readily apparent to one of ordinary skill in the art after reading this disclosure.

In particular, in step 210 a trigger signal of a timing of interest is obtained. In this regard, a "timing of interest" refers to any information corresponding to the display and/or analysis of images in accordance with a user's requirement based in whole or in part on a time of occurrence. By way of example, the trigger signal may comprise a periodic signal for triggering the display of images separated by a substantially equivalent period of time, a periodic or non-periodic signal corresponding to a physiological condition (e.g., a signal generated by an ECG probe sensing intra-cardiac electrical activity, an artificial heart stimulation signal generated by workstation 100, body movement detected electrically/optically/biochemically, etc.), a user selection-based signal (e.g., a user selecting a time point in a normal or abnormal heartbeat cycle) or any other trigger signal of a timing of interest. According to one aspect of the present invention, the trigger signal may be a complex and intermittently recurring ECG wave form, which requires analysis of a pattern to determine the presence of the complex signal (e.g., analysis of an ECG signal to determine the presence of an irregularity to be used as the trigger signal).

In step 220, a plurality of images of a feature of interest are obtained. By way of example, step 220 may comprise obtaining a plurality of intra-cardiac ultrasound images using ultrasound equipment 110 of FIG. 1. As will be described in greater detail below, step 220 may be performed prior to, concurrent with, or after step 210, depending upon the particular implementation at hand.

In step 230, the medical imaging system correlates or time gates (e.g., synchronize) the plurality of images obtained in step 220 with the trigger signal obtained in step 210. According to one aspect of the present invention, correlating or time gating in step 230 comprises utilizing the trigger signal obtained in step 210 to trigger generation of the plurality of images obtained in step 220. By way of example, ultrasound equipment 110 (FIG. 1) may generate ultrasound pulses correlated to the trigger signal—e.g., an ultrasound pulse may be generated once per cycle of a periodic trigger signal. In this manner, the obtained trigger signal is said to "time gate" the plurality of images, because the plurality of images are obtained (i.e., "gated") in accordance with a timing of interest. The result will be a series of images of structure (e.g., heart wall, heart valve, etc.) at the same point in the timed cycle (e.g., heart beat). If the structure cycles through repetitive motions, the series of images may be combined (e.g., added or averaged) to enhance the clarity, or compared to identify irregular motions. By sequentially varying a time lag following a particular (e.g., easily recognizable) timing, a series of images may be obtained of the structure at each of a number of intervals within the cycle. Thus, in the example of imaging a heart, the result may be a "movie" or "motion display" of an average heart cycle.

Alternatively, the images obtained in step 220 may be stored along with or indexed by associated timing information. It should be appreciated that "timing information" should be interpreted broadly as including any information that can be used to correlate the plurality of images with a timing of interest. Such information may include, for example, a time of occurrence (i.e., "X" image was taken at time "T"), a corresponding physiological condition (e.g., when "X" image was taken the measurement from ECG equipment 130 was "Y", or "X" image was taken simultaneous with a heartbeat), etc. In this manner, time gating in step 230 may comprise utilizing the trigger signal obtained in step 210 to retrieve images of interest (e.g., images taken at a timing of interest) from a database of stored images previously obtained in step 220 and stored by workstation 100. The retrieved images may then be combined or otherwise processed as herein described.

As described above, the present invention is applicable to time gating images in real-time, near real-time, or subsequent to image acquisition. However, the ability to trigger on individualized patient physiological patterns (e.g., using ECG equipment 130) provides valuable information for specific problems much more rapidly, compared to techniques that may require searching through data after the data is obtained in step 210. In an embodiment, specific imaging triggering based on real-time decision making provides improved data collection and even higher resolution images of sought after physiological events that may occur rarely or sporadically. In this embodiment, the system provides higher quality data by focusing system resources on the desired event, as determined by the user in real-time. For example, memory resources can be dedicated by workstation 100 to images that the user wants to see, alleviating the need to hunt through unneeded data, and also allows more efficient use of interventional energy by avoiding at least some unnecessary ultrasonic probing by equipment 110 and/or fluoroscopy by equipment 120. Thus, instead of continuously emitting ultrasonic or X-ray energy to obtain information, most of which may not be needed, the ultrasonic or X-ray energy output itself may be controlled by the trigger. Upon triggering, for example, the ultrasonic probe in equipment 110 can commence firing bursts of energy for a desired time period as previously described. Such even or time triggering of ultrasound or x-ray emitters may allow the use of higher energy pulses, such as to achieve deeper imaging, without increasing the total power or radiation deposited in the patient compared to continuous imaging. As such, the skilled user will appreciate the different features achievable using various teachings of the present invention.

According to another embodiment of the present invention, x-ray intensity may be controlled by a physiological trigger signal. For example, an ECG signal may gate a decrease, increase, switch on, or switch off x-ray generation by control of current to an electron beam used to generate x-rays within second imaging equipment 120. By way of example, a position on an ECG cycle may be used to trigger a change in x-ray intensity such as to turn on the beam to form an image at a particular point in the ECG cycle. An ultrasound scan and x-ray image may be made at the same time by co-triggering by the same ECG trigger signal.

According to yet another embodiment of the present invention, an x-ray scan may be triggered by motion or a shape obtained from ultrasound imaging equipment 110. This embodiment helps maximize system resources by time-focusing the use of diagnostic probes of a physiological state such as x-ray probes and ultrasound probes. This technique reduces exposure of body tissues to possible harmful radiation introduced by the imaging device.

The aforementioned techniques thus provide physicians with greater capabilities in medical imaging than in conventional devices, thereby allowing a physician to track a condition through a series of time events (e.g., tracking positions of catheters and tissue during an ablation procedure). Additional advantages may also be realized, particularly from the practice of additional embodiments described below in reference to FIGS. 3-5.

Figure 3:
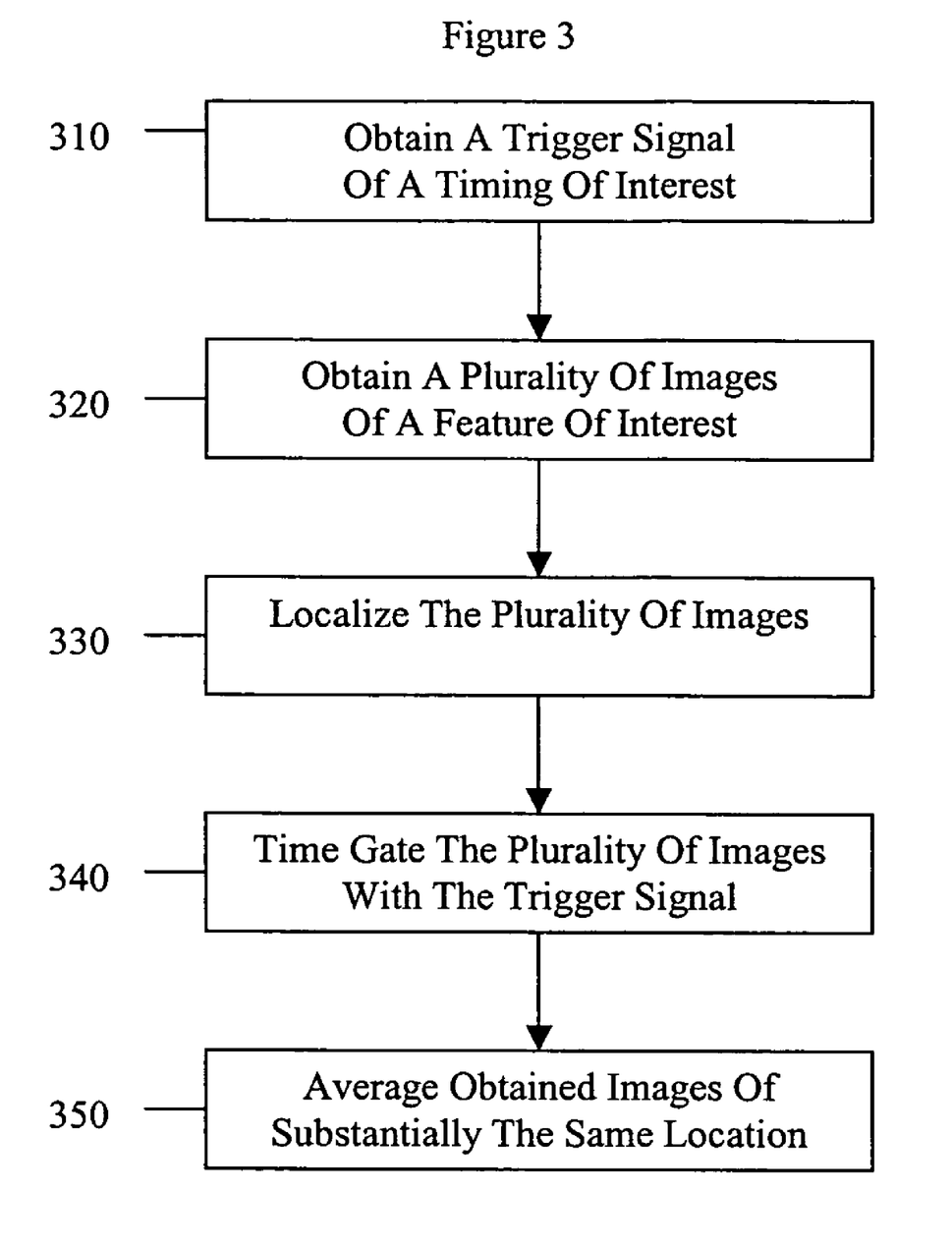
FIG. 3 is a flowchart of a method of time-gating medical images according to another embodiment of the present invention.

According to an embodiment of the present invention as shown in FIG. 3, noise reduction can be performed on a plurality of obtained images. To accomplish a reduction in such noise, a trigger signal of a timing of interest is obtained in step 310. A plurality of images of a feature of interest are then obtained in step 320 and localized (if necessary) in step 330. Localizing step 330 may be omitted, for example, if the imaging equipment (e.g., an ultrasound probe as part of equipment 110) remains focused on the same position while obtaining the images in step 320. Alternatively, localizing step 330 may utilize intra-body localizer equipment 140 to localize the plurality of images, as will be described in greater detail in subsequent embodiments.

In step 340, the plurality of images are time-gated to obtain multiple images in step 310 of substantially the same location at the same time-gate over a period of time. By way of example, the trigger signal obtained in step 310 may be used to obtain a plurality of images in step 320 of the same feature of interest (e.g., a heart valve), at the same cyclic point (e.g., closed) over a period of time (e.g., several heart beat cycles). These multiple images can then be averaged or combined in step 350 (e.g., by workstation 100) to provide an image having a greater signal to noise ratio than present in any single image as described more fully herein. By way of example, according to embodiments disclosed below, each pixel in a plurality of slides may be tracked and compared to a threshold occurrence level (e.g., number of images in which the pixel exceeds some threshold value) to eliminate spots that do not appear in at least a specified number of images. This comparison can minimize noise thereby enhancing the image, and the appearance of features of interest (e.g., the heart valve).

Figure 4:
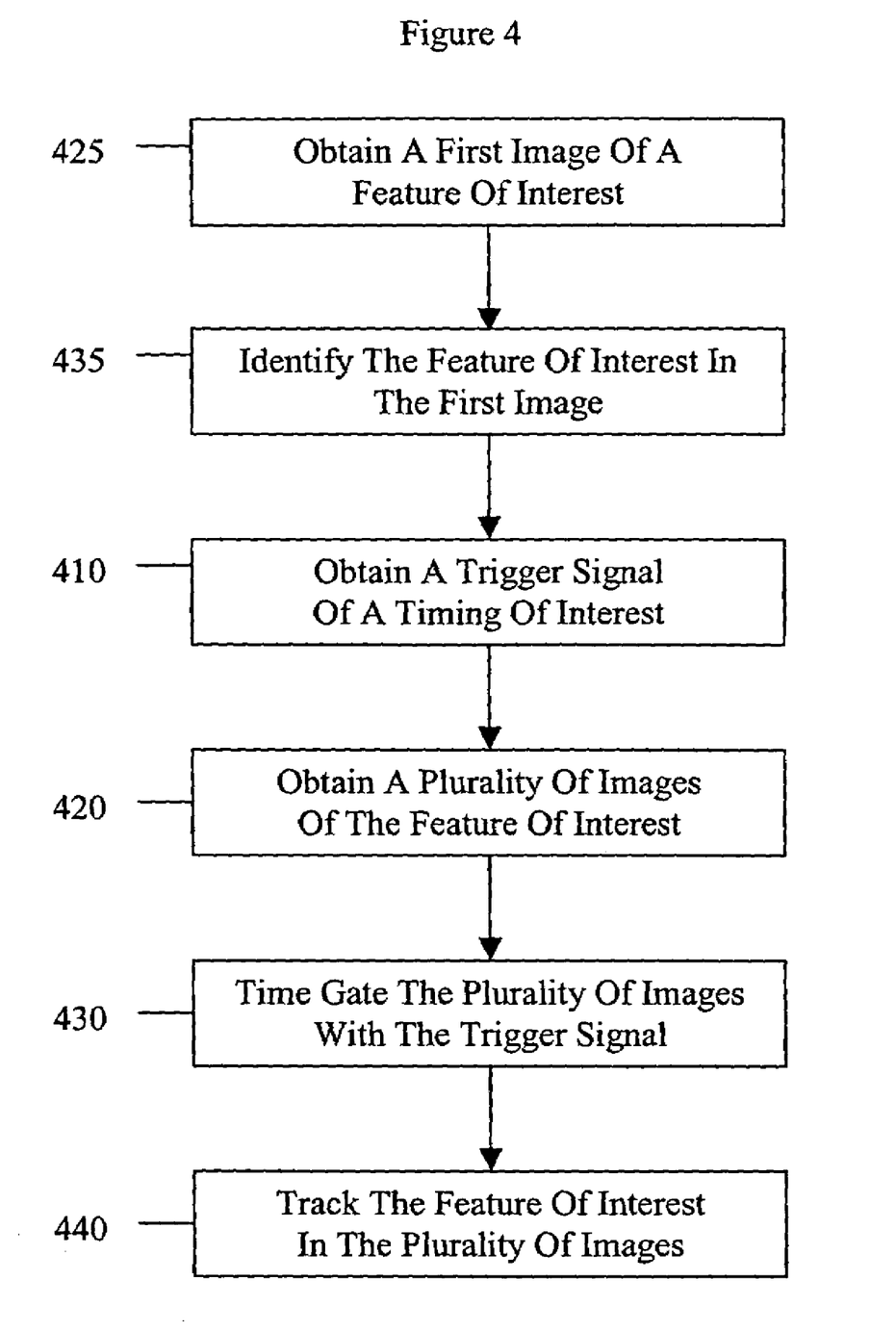
FIG. 4 is a flowchart of a method of time-gating medical images according to another embodiment of the present invention.

According to another embodiment of the present invention as shown in FIG. 4, the present invention may also be used to track movement of a feature of interest over time, also known as persistent image tracking in real-time. In particular, in step 425 a first image of a feature of interest is obtained. In step 435, the feature of interest in the first image is identified for tracking. By way of example, a user may highlight a heart valve on a display device as a feature of interest to be tracked over a series of images. Alternatively, workstation 100 may run an algorithm to identify one or more abnormal features, which can be automatically selected by the workstation 100 as the feature of interest.

In step 410 a trigger signal is then obtained of a timing of interest. By way of example, if a user identifies a heart valve as the feature of interest in step 435, the user may use the present embodiment to visualize the operation of a heart value over a period of time. In such an example, ECG equipment 130 is set to generate a trigger signal corresponding to the heart beat cycle which corresponds to the heart valve opening and closing, which is then time gated in step 430 to obtain the plurality of images of the feature of interest in step 420. Alternatively, the workstation 100 may parse stored images indexed to the trigger signal (e.g., ECG trace) to identify any later images corresponding to the same selected physiological/electrophysiological feature or event. The display device may be updated to show successive images of the same type of event. Thus, feature motion can then be tracked over a period of time corresponding to the timing of interest.

Additionally, similar to previous embodiments, successive images may be collated into a composite of progressively more data points averaged out into the composite for higher resolution. By way of example, if a heart valve is selected as the feature of interest, multiple images may be taken at a first heart valve position (e.g., an open position) and a second heart valve position (e.g., a closed position). In a like manner as described in reference to FIG. 3, multiple "first position" images may be averaged together, and multiple "second position" images may be averaged together, such that an aggregate "first position" and an aggregate "second position" are created. Thus, a high resolution "first position" and "second position" image may then be shown in succession to provide the user with a high resolution average motion display.

Figure 5:
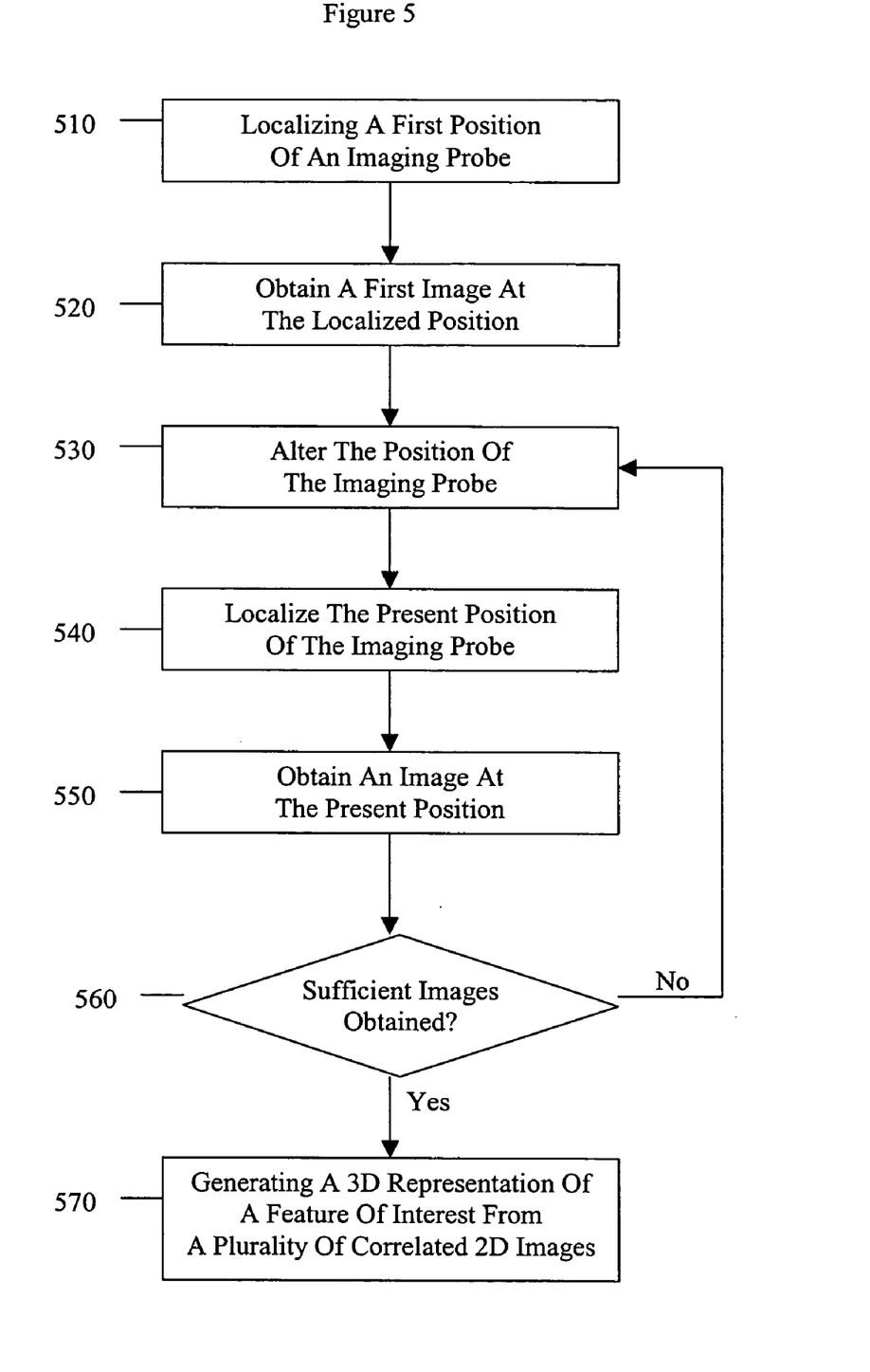
FIG. 5 is a flowchart of a method of time-gating medical images according to another embodiment of the present invention.

According to another embodiment of the present invention as shown in FIG. 5, the present invention may also be used to generate a still or moving 3D representation of a feature of interest from a plurality of correlated 2D images. More specifically, in step 510 the intra-body localizer equipment 140 (FIG. 1) is used to localize a position of an imaging probe (e.g., an intra-body ultrasound catheter probe forming part of ultrasound equipment 110). Such a process is described in co-pending application Ser. No. 10/994,424 entitled "Method And Apparatus For Localizing An Ultrasound Catheter" filed concurrently herewith, the entire contents of which is incorporated by reference herein in its entirety.

As one exemplary technique for performing step 510 (and step 540), the intra-body localizer equipment 140 may comprise one or more localizer transducers that are separated in space from imaging transducers, the localizer transducers generating signals for locating the position of the imaging transducers. For example, a piezoelectric transducer may be located at the opposite side of an axial catheter body from that of an ultrasound imaging array. By emitting signals and detecting reflection/interference of those signals on the opposite side from where the imaging sonic waves are used, the localizer transducer produces less interference with the imaging array. Preferably, a frequency range is chosen for the positional transducer that avoids or alleviates interference with the sonic waves of the imaging transducers.

Alternatively or in combination with the aforementioned technique, an ultrasound catheter (forming part of ultrasound equipment 110) may have one, two or more localization transducers at separate locations, such that the intra-body localizer equipment 140 can utilize triangulation techniques to determine the location of the imaging transducers on the ultrasound catheter. This may be used in conjunction with another measurable property, such as the ability to absorb (and/or re-emit) electromagnetic waves of different wavelengths to locate one, two, or more positional transducers, either separately from or in conjunction with the additional localizer transducers.

In one configuration, at least one, and advantageously at least two separately positioned transducers such as ultrasound transducers are introduced into the same body structure on positioning catheter(s) and used to determine the position of an imaging catheter. A process of triangulation may also be used in this technique to localize the imaging transducer thereon. Other techniques also exist for localization, as would be readily apparent to one of ordinary skill in the art after reading this disclosure. These techniques permit accurate localizing of an ultrasound imaging transducer in the six degrees of motion, namely spatial position (x, y, z) and orientation (pitch, yaw and roll), necessary to fix the images within a patient's body. Hence, the techniques described herein are presented for purposes of illustration only, and are not limiting on the scope of the present invention.

According to another embodiment of the present invention as shown in FIG. 5, the present invention may also be used to generate a still or moving 3D representation of a feature of interest from a plurality of correlated 2D images. More specifically, in step 510 the intra-body localizer equipment 140 (FIG. 1) is used to localize a position of an imaging probe (e.g., an intra-body ultrasound catheter probe forming part of ultrasound equipment 110). Such a process is described in co-pending application Ser. No. 10/994,424 entitled "Method And Apparatus For Localizing An Ultrasound Catheter" filed concurrently herewith, the entire contents of which is incorporated by reference herein in its entirety.

The intra-body localizer equipment 140 is then used to localize the present (i.e., second) position or orientation (i.e., after alteration in step 530) of the imaging catheter. In step 550, a subsequent image or series of images is obtained at the present location, and these images are stored along with the timing/triggering and localizing information as previously described. Steps 530, 540 and 550 are preferably repeated until images from a sufficient number of imaging perspectives have been obtained for 3D rendering (see step 560). According to one aspect of the present invention, steps 530, 540 and 550 are continued even after a 3D representation has been generated in step 570 in order to update/refresh the 3D representation with the latest images.

A 3D representation of a feature of interest may then be generated in step 570 by workstation 100 from the plurality of 2D images obtained in steps 520 and 550. The ultrasonic signals produced at each position often differ greatly but nevertheless can be massaged into similar images and matched up in accordance with known techniques.

In particular, according to one aspect of the present invention, a grid map of an internal body structure may be calculated by the workstation 100 from ultrasonic imaging using ultrasonic scan data obtained from an ultrasound imaging catheter or a portion of a multi-use catheter. A technique such as that described in U.S. Pat. No. 5,588,432, which is incorporated by reference herein in its entirety, may be used to generate acoustic data that form 3D images via appropriate computer software.

To depict a moving 3D image according to another aspect of the present invention, the method depicted in FIG. 5 is repeated for a given period of time. In this manner, a plurality of 3D images can be rendered over the given period of time. By way of example, a trigger signal, representing a point (e.g., an ECG peak or minimum) in a heartbeat cycle may be used to render a 3D image of a patient's heart (1) prior to, (2) concurrent with, and (3) subsequent to the point in the heartbeat. These three (or more) 3D images generated in step 570 (one per time sequence 1-3 in the heartbeat) may then be depicted in series as a 3D cinematic display, providing the user with a 3D image of the interior of the heart (e.g., a feature of interest) through the heartbeat.

In one example of this embodiment, a user may select 4D (3D plus time) images associated with a physiological anomaly, such as a strange ECG signal or other physiological signal, where the workstation 100 provides the user with a short span of video of the physiological anomaly. The user then can see how the imaged structure (such as a heart) progressively changed shape or behavior between earlier stored image copies of the image prior to the anomaly and later image copies during the anomaly.

While these examples illustrate use of the patient's own ECG signal as the physiological trigger signal for 4D generation, other physiological signal(s) may also be used that vary in synchrony or partial synchrony with the moving imaged structure, such as blood pressure, Doppler signal, a frame correlation coefficient, or even a feature (e.g., average gray-scale) from a region of interest in the image itself. Such signals may be merged and processed as a combined signal or selected independently and then the co-presence of the physiological signal may be used to select a cine. The period (repetition time) of the 3D image optionally may, of course, be predicted using other stored cycle duration time(s), such as a contraction of a single portion of a larger muscle.

According to another embodiment of the present invention, the plurality of images obtained in steps 520 and 550 may be reconciled with a visual guide such as a virtual grid map. This may, or may not be generated into a 3D representation in step 570, and thus has further uses other than for purely 3D generation.

To reconcile the grid map, the workstation 100 may apply a transform to at least one of the images and the map so that after transformation, the images and the map have a common axis and a common scale (i.e., the images and map are "registered"). In one embodiment, the image is divided further into multiple parallel planar slices, perpendicular to the axis and mutually spaced along the axis, wherein the plurality of image points are located in the slices. More advantageously, image registration with the map includes matching axial coordinates of each slice with an angular coordinate of each image point located in each slice, and identifying each image point with map points of similar axial and angular coordinates. In an embodiment, this registration is carried out on a structure by structure basis, such as vessel walls that define cavities, and each image point is identified with a map point. In an embodiment, this involves finding, at the axial and the angular coordinate, an image point that is within a section of the wall. To update position and/or allow registration of an ultrasonic derived image with the grid map, catheter positional information (e.g., steps 510 and 540) may be used.

Images that are reconciled with a grid map advantageously may be stored by workstation 100 as files with grid markings or other identifying information (e.g., indexing) to allow superimposition of images with a grid for readout display. In a desirable embodiment, the workstation 100 aligns two or more images, such as 2D images, 3D images, 3D images represented in a 2D form, or 4D images, and merges them into a single file of enhanced resolution compared to that of the images separately. In another embodiment, the images are merged after reconciliation with a grid map to format them with common landscape points.

In another embodiment, the images are merged after reconciliation using catheter position information (e.g., steps 510 and 540). One advantage of this latter embodiment is the lessened need for a high resolution map image such as that obtained by fluoroscopy at the same time as acquisition of an ultrasonic array derived image. Desirably, compounding with a finite impulse response (i.e. set time frame of the data point) is used for more versatile compositing. In this method, as described, for example, in U.S. Pat. No. 6,641,536 (which is incorporated by reference herein in its entirety), a device such as a computer (e.g., workstation 100) provides weighted averaging of a finite number of component images (e.g., frames of data). Infinite impulse response (i.e., recursive) compounding techniques also may be used, wherein each compounded frame overwrites or modifies the previously compounded pixel values from earlier frames based on the new pixel values. The 3D data also may be processed and displayed using a commercially available product, such as ViewMate, made by EP MedSystems, Inc. of West Berlin, N.J.

Desirably, the workstation 100 accepts user input to determine which physiological signal or pattern is to be used for selecting a 3D image or group of images (i.e. that form a 4D cinematic display). For example, the user may see a suspicious and non-periodic ECG pattern or graphical deflection and then select this on a touch screen display. The workstation 100, upon receiving this input searches a cine data bank for images that are correlated, linked or labeled with similar physiological signals. A new set of images that are associated with the same or similar physiological signal or pattern may be established by either noting their memory locations (indexing or making a file of the cine storage locations) or composing a new cine of the selected images. In a desirable embodiment, the collected images are averaged, summed or otherwise merged into a composite cine having a greater signal-to-noise ratio for improved viewing.

The collected images obtained according to the various embodiments may be compounded and processed by a variety of methods. One compounding method described in U.S. Pat. No. 6,014,473, involves interpolating data from boundary portions of different image data frames with variable weights. The weights applied to the image data frames vary linearly as a function of distance where the weights for one frame are one minus the weights for the other frame. Using these weights, one frame (or cine) in a collection is compounded with another frame (or cine) in the collection. Similarly, a "ramp compounding" method (see U.S. Pat. No. 5,575,286) may be used to give weight ramps for different images.

In another embodiment, speckle noise may be filtered from a compound image by combining a number of images in the following manner. Each point or pixel in the various images is inspected to determine if a value, or narrow range of values, is present in the pixel in more than one image. If the value (e.g., "0" indicating no echo) is present in a majority of images, a corresponding value is assigned to the pixel in the compound image. In this manner, a composite image can be assembled reflecting the most common structures present in the various images. The threshold percentage of the images containing a value required to set a corresponding pixel in the composite may be adjusted from, for example, a significant minority, to a simple majority to a supermajority as desired to reduce noise or increase sensitivity. Noise images, referred to as "speckle", will tend to be eliminated because they occur randomly in ultrasound images and therefore will not appear at a given pixel in a majority of images. Conversely, structure will tend to be enhanced in the composite image because echoes from structure will be received in a majority of images. Alternatively, the value assigned to a pixel may be based upon an average of the values for the pixel in the various images, with average values below an adjustable threshold set to zero to eliminate random speckle.

While the aforementioned embodiments have focused primarily on ultrasound imaging equipment 110, various embodiments are also applicable to second imaging equipment 120. As an example, medical x-ray systems usually operate at the lowest possible x-ray exposure level at the entrance of the patient that is consistent with image quality requirements. Unfortunately, contrast resolution and spatial resolution requirements for the procedure and the system being used require a minimum amount of ionizing radiation. However, an embodiment of the present invention alleviates this problem by improving contrast resolution and spatial resolution of the fluorometer derived image (typically a graphic outline) decreasing the need for high intensity x-radiation.

In this embodiment, positional sensor information and/or within sonic array image information contributes to the fluorometer derived image. By way of example, the outline of the body part (typically heart) obtained from the fluorometer may be stored in a file and updated as new information comes into the workstation 100. In this embodiment, extra data obtained from positional and sonic sensors (e.g., part of ultrasound equipment 110 or localizer equipment 140) can be used at least in part to create, verify, and/or amend the stored file, thereby decreasing the need for fluorometric data.

In one embodiment, a software subroutine continuously appraises the quality of the image and determines whether a higher rate of fluorometric data should be obtained to improve the image quality. The software controls the second imaging equipment 120, decreasing x-ray output when less data is needed, and increasing the output when more data is needed. For example, a more slowly moving target (scanned body) would be sensed and prompt a decrease in x-ray output. Analogously, intracardial spectral data output from an ultrasonic array would be analyzed and contribute to sharpening the same image. A software routine that detects image quality would test for quality after each update and subsequently increase or decrease the x-ray output. Of course, the image intensity of the fluorometer should be adjusted or compensated as well to correct for increasing and decreasing the image brightness.

The foregoing description of various embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments and with various modifications as are suited to the particular use contemplated.

What is claimed is:

1. A medical cardiac imaging system, comprising:
   a signal generator adapted and configured to obtain a signal from at least one electrocardiograph (ECG) sensor;
   imaging equipment comprising an intra-body ultrasound catheter having a linear phased array transducer adapted and configured to obtain a plurality of ultrasound images of a cardiac feature of interest; and
   a processor programmed with an operating mode adapted and configured to:
      receive the signal from the signal generator;
      analyze the signal to determine a presence of a particular complex and intermittently recurring ECG wave form;
      trigger the imaging equipment to obtain at least a plurality of images of the cardiac feature of interest upon determining the presence of the particular complex and intermittently recurring ECG wave form; and
      correlate the plurality of images with the signal.

2. The medical cardiac imaging system of claim 1, wherein the at least one electrocardiograph (ECG) sensor comprises an intra-cardiac electrocardiograph (ECG) sensor.

3. The medical cardiac imaging system of claim 1, wherein the processor is programmed to:
   store the plurality of images of the cardiac feature of interest and the signal;
   correlate stored images with the signal; and provide a 4-dimensional (4D) image spanning a duration of the particular complex and intermittently recurring ECG wave form.

4. The medical cardiac imaging system of claim 1, wherein the particular complex and intermittently recurring ECG wave form indicates atrial fibrillation.

5. The medical cardiac imaging system of claim 1, wherein the particular complex and intermittently recurring ECG wave form is selected from an ECG trace by a user.

6. A method of removing speckle noise from ultrasound medical images of a heart, comprising:
   obtaining a trigger signal of a timing of interest using at least one electrocardiogram (ECG) sensor;
   obtaining a plurality of ultrasound images of a feature of interest;
   correlating the plurality of images to select a subset of images associated with the timing of interest in the trigger signal;
   examining each point in each of the subset of images to determine if an echo is present at the point; and
   generating a composite image by assigning a pixel value to each point in the composite image if it is determined that an echo is present at the point in more than one image in the subset of images.

7. The method of removing speckle noise from ultrasound medical images of a heart of claim 6, wherein the pixel value is assigned to each point in the composite image if it is determined that an echo is present at the point in a significant minority of images in the subset of images.

8. The method of removing speckle noise from ultrasound medical images of a heart of claim 6, wherein the pixel value is assigned to each point in the composite image if it is determined that an echo is present at the point in a simple majority of images in the subset of images.

9. The method of removing speckle noise from ultrasound medical images of a heart of claim 6, wherein the pixel value is assigned to each point in the composite image if it is determined that an echo is present at the point in a super-majority of images in the subset of images.

10. The method of removing speckle noise from ultrasound medical images of a heart of claim 6, wherein the pixel value is assigned to each point in the composite image based upon an average of pixel values for the point in the subset of images, wherein if the average of pixel values for the point is below a threshold value the pixel value for the point is set to zero.

11. A software program resident on a computer readable medium containing instructions for causing a medical imaging system to perform steps of:
   obtaining a trigger signal of a timing of interest using at least one electrocardiogram (ECG) sensor;
   obtaining a plurality of ultrasound images of a feature of interest;

correlating the plurality of images to select a subset of images associated with the timing of interest in the trigger signal;

examining each point in each of the subset of images to determine if an echo is present at the point; and generating a composite image by assigning a pixel value to each point in the composite image if it is determined that an echo is present at the point in more than one image in the subset of images.

12. The software program of claim 11, wherein the pixel value is assigned to each point in the composite image if it is determined that an echo is present at the point in a significant minority of images in the subset of images.

13. The software program of claim 11, wherein the pixel value is assigned to each point in the composite image if it is determined that an echo is present at the point in a simple majority of images in the subset of images.

14. The software program of claim 11, wherein the pixel value is assigned to each point in the composite image if it is determined that an echo is present at the point in a supermajority of images in the subset of images.

15. The software program of claim 11, wherein the pixel value is assigned to each point in the composite image based upon an average of pixel values for the point in the subset of images, wherein if the average of pixel values for the point is below a threshold value the pixel value for the point is set to zero.

* * * * *